United States Patent [19]

Haviv et al.

[11] 4,273,940

[45] Jun. 16, 1981

[54] BIS-(2-BENZYLAMINOETHYL)-DISULFIDES

[75] Inventors: Fortuna Haviv, Vernon Hills; George W. Carter, Mundelein, both of Ill.

[73] Assignee: Abbott Laboratories, North Chicago, Ill.

[21] Appl. No.: 149,390

[22] Filed: May 13, 1980

Related U.S. Application Data

[63] Continuation-in-part of Ser. No. 86,854, Oct. 22, 1979, abandoned, which is a continuation-in-part of Ser. No. 962,513, Nov. 20, 1978, abandoned.

[51] Int. Cl.$^3$ ............................................. C07C 87/28
[52] U.S. Cl. .............................. 564/372; 260/501.18; 260/501.2; 424/316; 424/330; 564/272; 564/274; 568/425; 568/426
[58] Field of Search ......... 260/501.19, 501.2, 570.5 S; 424/316, 313; 564/372

[56] References Cited

U.S. PATENT DOCUMENTS

| | | | |
|---|---|---|---|
| 3,453,309 | 7/1969 | Westland | 260/570.5 X |
| 3,857,888 | 12/1974 | Kreider | 260/570.5 |
| 3,929,887 | 12/1975 | Fliedner, Jr. et al. | 260/570.5 |

OTHER PUBLICATIONS

Rachinski et al., "Chemical Abstracts", vol. 57, pp. 16585–16586, (1962).
Bruk et al., "Chemical Abstracts", vol. 74, p. 507, Section No. 49013y, (1971).

*Primary Examiner*—Robert V. Hines
*Attorney, Agent, or Firm*—Paul D. Burgauer; Robert L. Niblack

[57] ABSTRACT

It has been found that bis(2-benzylaminoethyl)-disulfides with the phenyl rings carrying various simple substituents, are highly effective anti-inflammatories and inhibit chemotaxis of human neutrophils.

16 Claims, No Drawings

BIS-(2-BENZYLAMINOETHYL)-DISULFIDES

HISTORY OF THIS APPLICATION

This application is a continuation-in-part of our previously filed application Ser. No. 06/086,854, filed Oct. 22, 1979, which is a continuation-in-part of Ser. No. 962,513, filed Nov. 20, 1978 both now abandoned.

DETAILED DESCRIPTION OF THE INVENTION

The present invention is directed to bis(2-benzylaminoethyl)disulfides of the formula

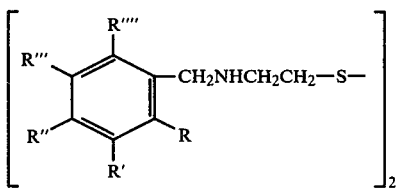

(hereinafter referred to as "disulfides"), wherein R and R'''' independently are hydrogen, hydroxy, halogen or loweralkyloxy, R' and R''' independently are hydrogen, halogen or loweralkyl and R'' is hydrogen or hydroxy, with the proviso that at least one of these substituents is different from hydrogen and loweralkyl, and nontoxic addition salts thereof.

The term "loweralkyl" is intended to include linear or branched hydrocarbons of 1 to 4 carbons.

The compounds of this invention show marked anti-inflammatory properties as intraperitoneal or oral doses of 25–200 mg./kg. and at intravenous doses of 10 mg./kg. and above. In this regard, the compounds of this invention are more effective as anti-inflammatories than acetylsalicylic acid. The current compounds also are inhibitors of chemotaxis of human neutrophils at molar concentrations of 0.00001–0.0005, causing 50–100% inhibition of intrinsic and chemotactic locomotion of the cells, as established by the method of Nelson et al. in J. Immunol. 115, 1650 (1975). This is a simple in vitro test for anti-inflammatories which shows the extent of inhibition for white blood cells to migrate.

In a simple embodiment, the compounds of Formula I are made by treating the benzaldehyde carrying the desired substituents R, R', R'' R''' and R'''' with bis(2-aminoethyl)disulfide and subsequently reducing the formed double bonds of the Schiff's bases with sodium borohydride or similar reducing agents that will not affect substituents carried on the phenyl rings. Obviously, the described reaction requires the use of two molar equivalents of the aldehyde per mole of disulfide, preferably an excess thereover.

In order to illustrate the method of manufacturing the compounds of Structure I, reference is made to the following examples which, however, are not meant to limit the invention in any respect. Wherever these examples mention two solvents for the crystallization procedure, the more polar was used to dissolve the compound and the other was added to induce crystallization.

EXAMPLE 1

A solution of 6.84 g. of 2-methoxybenzaldehyde and 3.8224 g. of bis(2-aminoethyl(disulfide in 1000 ml. of benzene was refluxed azeotropically overnight. The solution was concentrated in vacuo giving a colorless syrup residue. This was dissolved in ethanol and treated at room temperature with an ethanolic solution of 1.85 g. of sodium borohydride for 2 hours. Then an ethanol solution containing 9 ml. of concentrated hydrochloric acid was added dropwise until a pH of 3 is obtained. The formed white precipitate was removed by filtration. The filtrate was concentrated to half of its volume and ether was added. The precipitate was filtered and recrystallized from ethanol-ethyl acetate to produce 2.644 g. of pure bis(2-methoxybenzylaminoethyl)disulfide dihydrochloride; m.p. 183.5° C.

EXAMPLE 2

A solution of 5.85 g. of salicyl aldehyde and 3.6575 g. of bis(2-ethylamino)disulfide in 1000 ml. of benzene was refluxed azeotropically overnight. The solvent was removed under high vacuum giving a semicrystalline yellow compound, which was crystallized from cyclohexane to produce 6.02 g. of bis(2-hydroxybenzylideneaminoethyl)disulfide; m.p. 73°–74° C.

To a suspension of 4.86 g. of the preceding compound in ethanol was added dropwise a solution of 1.022 g. of sodium borohydride in ethanol over a period of 15 minutes at 0° C. The reaction mixture was stirred at room temperature for an additional 2 hours. The yellow color of the starting compound slowly disappeared and a white precipitate was formed. This was filtered to give 2.22 g. of a crude product. The filtrate was concentrated and washed with water to give an additional 2.26 g. of the same crop. Both crops were crystallized from cyclohexane to give 3.12 g. of bis(2-hydroxybenzylaminoethyl)disulfide; m.p. 100°–102° C.

EXAMPLE 3

A solution of 12.22 g. of 3,5-dibromosalicyl aldehyde and 3.316 g. of bis(2-aminoethyl)disulfide in 1000 ml. of benzene was refluxed azeotropically overnight. The solvent was removed in vacuo and the product was crystallized from chloroform-petroleum ether. It gave 9.516 g. of (2-hydroxy-3,5-dibromobenzylideneaminoethyl)disulfide; m.p. 155°–157° C.

To a suspension of 6.835 g. of this product in ethanol was added dropwise a solution of 0.765 g. of sodium borohydride in ethanol at 0° C. The yellow color of the starting compound slowly disappeared and a white precipitate was formed. The reaction mixture was stirred for 2 hours at room temperature. The precipitate was filtered and subsequently treated with ethanol containing 1.59 ml. of concentrated hydrochloric acid. The compound dissolved and slowly, the hydrochloride salt precipitated. It gave 4.68 g. of bis(2-hydroxy-3,5-dibromobenzylaminoethyl)disulfide dihydrochloride; m.p. 224°–225° C.

EXAMPLE 4

A solution of 16.4 g. of 2-methyl-4-t-butylphenol and 14 g. of hexamethylenetetramine in 150 ml. of trifluoroacetic acid was refluxed for 6 hours. An exothermic reaction was observed when the reagents were mixed. The solution became dark on heating. After refluxing, 150 ml. of concentrated HCl and 50 ml. of water was added dropwise and reflux was continued for 0.5 hours. The reaction mixture was cooled and the precipitate was isolated by filtration. The filtrate was concentrated in vacuo and the obtained residue was dissolved in methylene chloride and washed with water. The organic phase was dried over anhydrous sodium sulfate and concentrated. The obtained red-brown oil was distilled, giving 7.2 g. of 3-methyl-5-t-butylsalicyl aldehyde; b.p. 90°–100° C./0.2 mm Hg.

A solution of 5.43 g. of 3-methyl-5-t-butylsalicyl aldehyde and 2.15 g. of bis(2-aminoethyl)disulfide in 1000 ml. of benzene was refluxed azeotropically overnight. The solvent was removed in vacuo and the residue was extracted with hot hexane-cyclohexane. The solution was concentrated to give 7.2 g. of a semi-solid identified as bis(2-hydroxy-3-methyl-5-t-butylbenzylideneaminoethyl) disulfide. This was dissolved in 100 ml. of ethanol and treated with a solution of 1.08864 g. of sodium borohydride in 250 ml. of ethanol at room temperature for 2 hours. Ethanol containing 4 ml. of concentrated HCl was added dropwise until the pH was adjusted to 3.5. A white precipitate was formed and removed by filtration. The filtrate was concentrated and crystallized from ethanol-ethyl acetate. It gave 4.43 g. of bis(2-hydroxy-3-methyl-5-t-butylbenzylaminoethyl)disulfide dihydrochloride; m.p. 200°–201° C.

EXAMPLE 5

In analogy to the preparation of the substituted salicylaldehyde in Example 4, 3-chloro-5-t-butylsalicyl aldehyde (m.p. 69°–71° C.) was prepared from 2-chloro-4-t-butylphenyl. A solution of 3.837 g. of 5-t-butyl-3-chlorosalicyl aldehyde and 1.375 g. of bis(2-aminoethyl)disulfide in 1000 ml. of benzene was refluxed azeotropically overnight. The solvent was removed in vacuo and the residue was crystallized from hot hexane, producing 2.17 g. of bis(2-hydroxy-3-chloro-5-t-butylbenzylideneaminoethyl)disulfide; m.p. 143°–145° C.

To a suspension of 1.44 g. of the above in ethanol was added dropwise a solution of 0.2018 g. of sodium borohydride in ethanol at 0° C. The mixture was stirred for 1.5 hours which dissolved the starting material. A white precipitate formed slowly; it was filtered giving 0.633 g. of crude product. The filtrate was concentrated and the residue was washed with water, giving an additional 0.519 g. of the compound. Both crops were combined and crystallized from cyclohexanehexane (1:1 by vol.) giving 0.82 g. of bis(2-hydroxy-3-chloro-5-t-butylbenzylaminoethyl)disulfide; m.p. 116°–117° C.

EXAMPLE 6

A solution of 13.468 g. of 2,6-dichlorobenzaldehyde was treated with 5.85 g. of bis(2-aminoethyl)disulfide in 1000 ml. of benzene containing 1 ml. of acetic acid and refluxed azeotropically overnight. The solution was then washed first with an aqueous sodium bicarbonate and then with an aqueous NaCl solution, dried and concentrated to a syrup. The latter was dissolved in 200 ml. of ethanol and reduced with 2.66 g. of sodium borohydride in 600 ml. of ethanol at room temperature for 2 hours. After adjusting the pH to 3.5 and work-up as before, bis(2,6-dichlorobenzylaminoethyl)disulfide hydrochloride is obtained. Upon recrystallization from ethyl acetate-ether, it melts at 198°–200° C.

EXAMPLE 7

A solution of 9.36 g. of 3,5-di-t-butyl-4-hydroxy benzaldehyde was treated with 3.04 g. of bis(2-aminoethyl)-disulfide in the above fashion,, producing a yellow powder which crystallizes from chloroform-cyclohexane to give 8.5 g. of bis(3,5-di-t-butyl-4-hydroxybenzylideneaminoethyl)disulfide.

A suspension of 8.5 g. of the above disulfide in 200 ml. of ethanol was treated with 2.05 g. of sodium borohydride and worked up as in the preceding examples, producing bis(3,5-di-t-butyl-4-hydroxybenzylaminoethyl)disulfide.

The new compounds have anti-inflammatory activity and inhibitory effects in the Type III hypertensive reaction and on polymorphonuclear leukocytes locomotion. Therefore, the compounds of Structure I are useful for treating rheumatoid arthritis, other inflammatory conditions, Type III hypersensitivity disease, and they can be used in treating diseases in which polymorphonuclear leukocyte accumulation contributes to pathology.

The anti-inflammatory activity of the current disulfides is established using a modification of the carrageenin induced hind paw edema assay described by Winter et al. (Proc. Soc. Exp. Biol. Med. 111, 544 of 1962). An intraperitoneal dose of 50 mg./kg. of the compound of Example 1 reduces the carrageenin induced swelling by 29.9% of its volume after 3 hours. The same 3 hour figure, after intraperitoneal administration at 25 mg./kg. produced a reduction of 14.6%. The corresponding measurement for acetylsalicylic acid at 50 mg/kg. produces only a 15.4% reduction.

As mentioned above, the current compounds also inhibit the Type III hypertensive reactions. This is demonstrated by using the reverse passive Arthus assay, as described by Carter and Krause (Fed. Proceed. 35, 744 of 1976). Upon intraperitoneal administration to a group of four animals at a dose of 50 mg./kg., the lesion area is inhibited an average of 49% by the compound of Example 1 and 47% by the compound of Example 5.

By carrying out the in vitro test of Nelson et al. referred to above, the neutrophil locomotor response modification caused by the above compounds was established. For this purpose, the compounds were dissolved in both agarose media and the media suspending the cells. The effects of the compounds were determined by comparing te chemotactic and intrinsic locomotion of the cells, both with and without the test compounds after 2 hours of incubation at 37° C. All compounds were evaluated in duplicate against the cells which were from four individual donors. Table I below shows the effects on intrinsic and chemotactic inhibition of locomotion at the indicated molar concentration.

TABLE I

| Compound | Molar Concentration | % Inhibition of Locomotion | |
|---|---|---|---|
| | | Intrinsic | Chemotactic |
| 1 | $10^{-4}$ | 100 | 100 |
| 1 | $10^{-5}$ | 94 | 93 |
| 2 | $10^{-4}$ | 100 | 100 |
| 4 | $10^{-4}$ | 95 | 100 |
| 4 | $10^{-5}$ | 50 | 48 |
| 5 | $10^{-4}$ | 85 | 100 |
| 5 | $10^{-5}$ | 24 | 46 |
| 6 | $10^{-4}$ | 74 | 85 |

The compounds of the present invention are preferably used in oral dosage forms such as tablets, capsules, wafers, elixirs, syrups and the like. For liquid forms, the above compounds are suspended in an aqueous medium containing the customary flavoring and coloring agents. Since these compounds are essentially insoluble in water, dispersing and/or suspending agents acceptable for human consumption are used together with suspension stabilizers. For the various solid dosage forms, the usual solid diluents are used where required. Capsules can be filled with undiluted powdered or granulated crystals of the new compounds. For tablets, the following standard procedure may be used:

A blend of 51.5 g. of cornstarch and 500 g. of the compound of Structure I is milled until homogenous and passed through a 40-mesh screen. This blend is granulated with a solution of 15 g. of polyvinylpyrrolidone in alcohol or water and subsequently dried in a hot air oven at 50° C. and sifted through a 16-mesh screen. The obtained granules are then mixed with 10 g. of talcum powder, 2.5 g. of magnesium stearate and 1.0 g. of combined coloring and flavoring additives. The mixture is blended to homogeneity, passed through a 30-mesh screen and blended for another 15 minutes. This blend is compressed into tablets weighing approximately 580 mg. using a ½" standard round convex punch resulting in tablets of a hardness of 7-9 with each tablet containing 500 mg. of the drug. In a similar fashion, tablets weighing 830 mg. containing 750 mg.. of drug can be prepared, preferably in a tableting machine producing bisected tablets.

A practical range for daily oral administration is between 10 and 200 mg./kg. with a preferred range being 25-100 mg./kg. These amounts are based on the free disulfide. However,, it is to be understood that pharmaceutically acceptable acid addition salts can be used in place of the free disulfide, e.g., the hydrochloride, sulfate, phosphate, citrate, succinate, acetate and the like.

Liquid dosage forms are prepared in known manner by dissolving the desired nontoxic acid addition salt of the compound of Structure I in the desired amount of sterile water. As it is well known in the art, stabilizers, buffers, preservatives and the like can be added to extend the storage life of solutions. Solutions of this nature are preferably prepared in concentrations of 10-50% of the above free base, but using the corresponding amount of a nontoxic addition salt thereof. When, for instance, a practical concentration of 25% of the compound of Structure I is used, a single adult dose of 1.2 ml. delivers 300 mg. or about 5 mg./kg. to said adult for intraperitoneal, intramuscular or subcutaneous injections.

We claim:

1. A compound of the formula

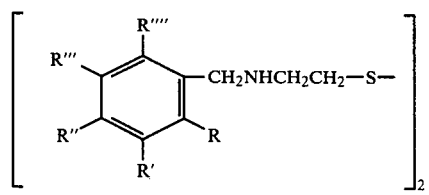

wherein R and R"" independently are hydrogen, hydroxy, loweralkyloxy or halogen, R' and R'" independently are hydrogen, halogen or loweralkyl, and R" is hydrogen or hydroxy, with the proviso that at least one of these substituents is different from hydrogen or loweralkyl, or a nontoxic acid addition salt thereof.

2. The compound of claim 1 wherein R is methoxy and R', R", R'" and R"" are hydrogen, or a salt thereof.

3. The compound of claim 1 wherein R is hydroxy and R', R", R'" and R"" are hydrogen, or a salt thereof.

4. The compound of claim 1 wherein R is hydroxy, R' and R'" are bromine and R" and R"" are hydrogen, or a salt thereof.

5. The compound of claim 1 wherein R is hydroxy, R" and R'" are hydrogen, R' is chlorine and R"" is t-butyl, or a salt thereof.

6. The compound of claim 1 wherein R is hydroxy, R" and R"" are hydrogen, R' is methyl and R'" is t-butyl, or a salt thereof.

7. The compound of claim 1 wherein the phenyl rings carry chlorine in the 2- and 6-positions, or a salt thereof.

8. The compound of claim 1 wherein R' and R'" are t-butyl, R" is hydroxy and R and R"" are hydrogen or a salt thereof.

9. A composition for alleviating symptoms of inflammations in dosage form containing, as the active principal thereof, a compound of the formula

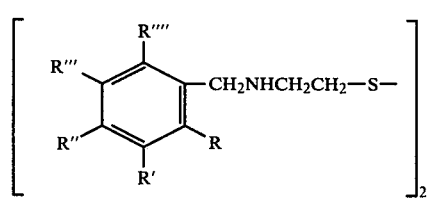

wherein R and R"" independently are hydrogen, hydroxy, loweralkyloxy or halogen, R' and R'" independently are hydrogen, halogen or loweralkyl, and R" is hydrogen or hydroxy, with the proviso that at least one of these substituents is different from hydrogen or loweralkyl, or a nontoxic acid addition salt thereof.

10. The composition of claim 9 wherein R is methoxy and R', R", R'" and R"" are hydrogen, or a salt thereof.

11. The composition of claim 9 wherein R is hydroxy and R', R", R'" and R"" are hydrogen, or a salt thereof.

12. The composition of claim 9 wherein R is hydroxy, R' and R'" are bromine and R" and R"" are hydrogen, or a salt thereof.

13. The composition of claim 9 wherein R is hydroxy, R" and R"" are hydrogen, R' is chlorine and R'" is t-butyl, or a salt thereof.

14. The composition of claim 9 wherein R is hydroxy, R" and R"" are hydrogen, R' is methyl and R'" is t-butyl, or a salt thereof.

15. The composition of claim 9 wherein the phenyl rings carry chlorine in the 2- and 6-positions, or a salt thereof.

16. The composition of claim 9 wherein R' and R'" are t-butyl, R" is hydroxy and R and R"" are hydrogen, or a salt thereof.

* * * * *